United States Patent
Buettgen et al.

(10) Patent No.: US 7,033,803 B1
(45) Date of Patent: Apr. 25, 2006

(54) PROCESS FOR THE PRODUCTION OF DEACIDIFIED TRIGLYCERIDES

(75) Inventors: Karl-Heinz Buettgen, Kerpen (DE); Manfred Lindemann, Solingen (DE); Daniela Prinz, Monheim (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 852 days.

(21) Appl. No.: 09/717,894

(22) Filed: Nov. 21, 2000

(30) Foreign Application Priority Data

Nov. 25, 1999 (DE) ................................. 199 56 599

(51) Int. Cl.
*C12P 7/62* (2006.01)
*C12P 7/64* (2006.01)

(52) U.S. Cl. ...................... 435/134; 435/135; 435/198; 554/167

(58) Field of Classification Search ................ 435/134, 435/135, 198; 554/167
See application file for complete search history.

(56) References Cited

U.S. PATENT DOCUMENTS

| | | | |
|---|---|---|---|
| 4,608,202 A | * | 8/1986 | Lepper .................. 554/167 |
| 5,514,820 A | | 5/1996 | Assmann et al. |
| 5,753,473 A | * | 5/1998 | Gatfield ................. 435/135 |

FOREIGN PATENT DOCUMENTS

| | | |
|---|---|---|
| DE | 39 32 514 | 4/1991 |
| JP | 4-183396 | 6/1992 |

OTHER PUBLICATIONS

Miller, et al., "Characteristics of an Immobilized Lipase for the Commercial Synthesis of Esters", JAOCS, vol. 65, No. 6, (Jun., 1988), pp. 927-931.
Ramamurthi, et al., "Lipase-Catalyzed Esterification of Oleic Acid and Methanol in Hexane-A Kinetic Study", JAOCS, vol. 71, No. 9, (Sep., 1994), pp. 927-930.

* cited by examiner

*Primary Examiner*—Irene Marx
(74) *Attorney, Agent, or Firm*—Daniel S. Ortiz; John F. Daniels

(57) ABSTRACT

Deacidified fats and/or oils are made by the process which comprises the steps of:
(a) reacting a technical triglyceride having an acid value of up to about 60 and a stoichiometric excess of a lower alcohol having from 1 to 4 carbon atoms and from about 0.5% to about 5% by weight of a lipase to form a pre-esterification product having an acid value of from about 0.5 to about 10,
(b) optionally removing water and unreacted alcohol from the pre-esterification product,
(c) further reacting the pre-esterification product from step (a) or (b) with additional lower alcohol to form a post-esterification reaction product having an acid value of from about 0.1 to about 0.5.

10 Claims, No Drawings

PROCESS FOR THE PRODUCTION OF DEACIDIFIED TRIGLYCERIDES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates generally to oleochemical raw materials and more particularly to a process for the enzymatic deacidification of natural fats and oils.

Native fats and oils normally contain considerable quantities of fatty acids as a result of enzymatic degradation reactions, their fatty acid content being variable within wide limits according to provenance and previous history, but almost always exceeding 3% by weight. These free fatty acids have been found to be troublesome in the various processes used for further processing of the triglycerides, more especially in the low-pressure transesterification process for the production of fatty acid methyl esters. Accordingly, it is normally not possible to avoid converting the fatty acids into alkyl or glycerol esters by refining or preliminary esterification with lower alcohols. However, this is very time- and energy-consuming, especially since large excesses of alcohol have to be used and the necessary catalysts are difficult to remove.

Accordingly, the problem addressed by the invention was to provide a new process for the deacidification of fats and oils which would be free from the disadvantages mentioned.

BRIEF SUMMARY OF THE INVENTION

Deacidified fats and/or oils are made by the process which comprises the steps of:
(a) reacting a technical triglyceride having an acid value of up to about 60 and an excess of a lower alcohol having from 1 to 4 carbon atoms and an effective amount of a lipase to form a pre-esterification product having an acid value of from about 0.5 to about 10,
(b) optionally removing water and unreacted alcohol from the pre-esterification product,
(c) further reacting the pre-esterification product from step (a) or (b) with additional lower alcohol to form a post-esterification reaction product having an acid value of from about 0.1 to about 0.5.

BRIEF DESCRIPTION OF THE SEVERAL VIEWS OF THE DRAWING

Not Applicable.

DETAILED DESCRIPTION OF THE INVENTION

The present invention relates to a process for the production of deacidified fats and/or oils, in which
(a) technical triglycerides with acid values of up to 60 are treated with an excess of lower aliphatic alcohols in the presence of an effective amount of a lipase to form a pre-esterification product which still has an acid value of 0.5 to 10,
(b) water and unreacted alcohol are optionally removed from the pre-esterification product,
(c) the optionally dried pre-esterification product is subjected in the presence of more lower aliphatic alcohol to a post-esterification reaction in which the acid value of the starting materials is reduced to 0.1 to 0.5.

It has surprisingly been found that the acid values of even particularly acidic fats and oils can be reduced quickly, reliably and with minimal outlay on equipment to below 0.5 by the process according to the invention so that starting materials thus refined are eminently suitable for use as such, i.e. without further purification, in the low-pressure transesterification process described, for example, in German Patent application DE-A1 3932514.

Triglycerides

Basically, the choice of the fats and oils to be deacidified is not critical. The triglycerides normally used correspond to formula (I):

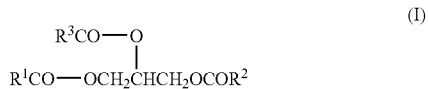

in which $R^1CO$, $R^2CO$ and $R^3CO$ independently of one another represent linear and/or branched, saturated and/or unsaturated acyl groups containing 6 to 24 and preferably 12 to 18 carbon atoms and 0 and/or 1 to 3 double bonds. From their production, the starting materials contain significant quantities of free fatty acids, so that they can have acid values of up to 60 and preferably in the range from 15 to 50. In consequence of the partial saponification, the triglycerides may also contain corresponding quantities of partial glycerides, i.e. mono- and diglycerides. The process according to the invention may employ naturally occurring or synthetic triglycerides or a combination thereof. The preferred triglycerides are natural fats and oils such as, for example, palm oil, palm kernel oil, olive oil, olive kernel oil, sunflower oil from old and new plants, rapeseed oil from old and new plants, linseed oil, soybean oil, bovine tallow and fish oil. However, it is preferably applied to technical coconut oils which have acid values of from about 15 to about 60. If only mildly acidic fats and oils are used, the acid value can be raised to a maximum of about 60 and preferably about 20 by the addition of free fatty acids, for example refining fatty acids. In this way, the quantity of alkyl ester is optimized and the process made particularly economical.

Aliphatic Alcohols

Basically, suitable lower aliphatic alcohols which are added to and mixed with the triglycerides during the pre- and the post-esterification steps are those containing 1 to 4 carbon atoms, i.e. for example ethanol, propanol, isopropyl alcohol and the isomeric butanols. However, the deacidified triglycerides are normally transesterified to the fatty acid methyl esters which are then hydrogenated to the fatty alcohols. Accordingly, the preferred alcohol is methanol. The quantities of alcohol which can be used in steps (a) and (c) is an excess amount so that, preferably, additions of from about 1 to about 10% by weight and preferably from about 3 to about 8% by weight, based on the triglycerides, in each of the two steps have proved successful.

Lipases

The use of lipases for the esterification of fatty acids with alcohols is well-known. From the wealth of prior art literature available on the subject, reference is made purely by way of example at this juncture to the two articles in J. Am. Oil Chem. Soc. 65, 927 (1988) and ibid. 71, 927 (1994). The reduction of the acid value by pre-esterification with glycerol is the subject of Japanese patent application JP Hei 04/183396. The choice of the lipases used for the pre- and post-esterification steps is again not critical. Basically, any of the representatives known from the literature, such as for example *Candida cylindracea, Aspergillus niger* or *Pseudomonas fluorescens*, may be used. However, *Candida antarctica* has proved to be particularly effective. The quantity of lipases used is an effective amount which is any amount required to bring about the desired acid value. Typically, the amount of the lipase will be between about 0.5 and about 5% by weight of the triglyceride and is preferably from about 2 to about 4% by weight, based on the triglycerides, a substantially linear increase in the reaction rate being observed up to a quantity of about 4% by weight.

Pre- and Post-Esterification The pre- and post-esterification steps may be carried out in known manner. The acidic fats and oils are mixed with the lipase and the lower alcohols, optionally with stirring. The pre-esterification temperature may be from about 10 to about 50° C. but is preferably in the range from about 20 to about 40° C. Once the product has reached an acid value of from about 0.5 to about 10, which can readily be established by sampling, the water of reaction formed is removed in a preferred embodiment of the invention in order to enable the equilibrium to be shifted further to the product side in the post-esterification. At the same time, the unreacted alcohol is at least partly removed but may be returned to the reaction later after working up. The removal of water may be dispensed with providing the quantity of enzyme is sufficiently large, for example of the order of about 4% by weight. Under these conditions, pre- and post-esterification coincide. A second quantity of the alcohol is then added to the mixture optionally freed from water beforehand. The post-esterification is carried out under the same conditions as the pre-esterification and is terminated when the required acid number has been reached. The small quantities of water formed in the post-esterification may remain in the end product together with the unreacted alcohol and the lipase because they do not affect the subsequent low-pressure transesterification.

The following examples are meant to illustrate but not to limit the invention.

EXAMPLE 1

To crude coconut oil with an acid value of 8.2 were added 2% by weight—based on the triglyceride—of commercially available lipase of the *Candida antarctica* type (NOVOZYM® 435) and 5% by weight—again based on the triglyceride—of methanol, followed by stirring at 30° C. After 1 hour, an acid value of 1.05 had been reached. The water of reaction was then distilled off in vacuo together with the unreacted alcohol and another 5% by weight of methanol was added to the mixture remaining behind. The mixture was then stirred for another hour at 30° C. and post-esterified at the same time, the acid value falling to 0.41.

EXAMPLE 2

Example 1 was repeated using 4% by weight of lipase; the water of reaction was not removed. An acid value of 0.5 was reached after a reaction time of only 1 hour.

What is claimed is:

1. A process for the production of deacidified fats and/or oils comprising the steps of:
   (a) reacting a triglyceride having an acid value of up to about 60 and an excess of a lower alcohol having from 1 to 4 carbon atoms and an effective amount of a lipase to form a pre-esterification product having an acid value of from about 0.5 to about 10,
   (b) optionally removing water and unreacted alcohol from the pre-esterification product,
   (c) further reacting the pre-esterification product from step (a) or (b) with additional lower alcohol to form a post-esterification reaction product having an acid value of from about 0.1 to about 0.5.

2. The process of claim 1 wherein the triglyceride is a compound of the formula (I):

wherein each of $R^1CO$, $R^2CO$ and $R^3CO$ is a linear and/or branched, saturated and/or unsaturated acyl group having from 6 to 24 carbon atoms and having up to 3 double bonds.

3. The process of claim 1 wherein the triglyceride is a synthetic triglyceride, a natural triglyceride or a combination thereof.

4. The process of claim 1 wherein the triglyceride is coconut oil having an acid value of from about 15 to about 60.

5. The process of claim 1 wherein the acid value of the triglyceride is increased to a maximum acid value of about 60 by the addition of a fatty acid.

6. The process of claim 1 wherein the lower alcohol is methanol.

7. The process of claim 1 wherein the amount of the lower alcohol is from about 1 to about 10% by weight of the triglyceride.

8. The process of claim 1 wherein the lipase is *Candida antarctica*.

9. The process of claim 1 wherein the amount of the lipase is from about 0.5 to about 5% by weight of the triglyceride.

10. The process of claim 1 wherein steps (a) and (c) are each carried out at a temperature of from about 10 to about 50° C.

* * * * *